(12) United States Patent
Kim et al.

(10) Patent No.: US 12,247,250 B2
(45) Date of Patent: Mar. 11, 2025

(54) POINT OF NEED TESTING DEVICE AND METHODS OF USE THEREOF

(71) Applicants: GODX, INC, Madison, WI (US); THE UNITED STATES OF AMERICA, AS REPRESENTED BY THE SECRETARY, DEPARTMENT OF HEALTH & HUMAN SERVICES, Bethesda, MD (US)

(72) Inventors: Chang Hee Kim, Waunakee, WI (US); Wendy A. Henderson, Bethesda, MD (US); Sarah K. Abey, Bethesda, MD (US); Nicolaas H. Fourie, Bethesda, MD (US); Eric G. Ferguson, Bethesda, MD (US)

(73) Assignees: GODX, INC, Madison, WI (US); THE UNITED STATES OF AMERICA, AS REPRESENTED BY THE SECRETARY, DEPARTMENT OF HEALTH & HUMAN SERVICES, Bethesda, MD (US)

(*) Notice: Subject to any disclaimer, the term of this patent is extended or adjusted under 35 U.S.C. 154(b) by 1106 days.

(21) Appl. No.: 16/941,333

(22) Filed: Jul. 28, 2020

(65) Prior Publication Data
US 2020/0354778 A1    Nov. 12, 2020

Related U.S. Application Data

(62) Division of application No. 15/574,750, filed as application No. PCT/US2016/032788 on May 16, 2016, now abandoned.
(Continued)

(51) Int. Cl.
C12Q 1/6834    (2018.01)
B01L 3/00    (2006.01)
(Continued)

(52) U.S. Cl.
CPC .......... *C12Q 1/6834* (2013.01); *B01L 3/5023* (2013.01); *C12Q 1/00* (2013.01);
(Continued)

(58) Field of Classification Search
CPC .............. B01L 2400/0406; C12Q 1/00; C12Q 2565/625; C12Q 1/6834
See application file for complete search history.

(56) References Cited

U.S. PATENT DOCUMENTS

| 5,310,650 A | 5/1994 | McMahon |
| 6,037,127 A | 3/2000 | Ebersole |

(Continued)

FOREIGN PATENT DOCUMENTS

| WO | 2010102294 A1 | 9/2010 |
| WO | 2013036913 A1 | 3/2013 |

OTHER PUBLICATIONS

Gao et al., "Visual detection of microRNA with lateral flow nucleic acid biosensor," Biosensors and Bioelectronics, available on-line Nov. 25, vol. 54, pp. 578-584. (Year: 2013).*
(Continued)

*Primary Examiner* — Young J Kim
(74) *Attorney, Agent, or Firm* — Quarles & Brady, LLP

(57) ABSTRACT

The present invention relates to the rapid and electricity-free, point-of-care, multiplexed detection and quantification of at least one or more nucleic acid sequences from nucleic acids corresponding to a plurality of pathogens or biomarkers using a micropatterned lateral flow device. Rapid and molecular-level sensitive differential diagnosis of a disease condition may be enabled without the need for a delayed laboratory test so that timely treatment can be administered.

12 Claims, 6 Drawing Sheets

Specification includes a Sequence Listing.

Related U.S. Application Data

(60) Provisional application No. 62/162,668, filed on May 16, 2015.

(51) Int. Cl.

| | |
|---|---|
| *C12Q 1/00* | (2006.01) |
| *C12Q 1/6816* | (2018.01) |
| *C12Q 1/6825* | (2018.01) |
| *C12Q 1/6888* | (2018.01) |
| *C12Q 1/689* | (2018.01) |
| *C12Q 1/70* | (2006.01) |
| *G01N 15/06* | (2006.01) |
| *G01N 15/10* | (2006.01) |
| *G01N 15/14* | (2006.01) |
| *G01N 15/1433* | (2024.01) |
| *G01N 33/487* | (2006.01) |
| *G01N 15/075* | (2024.01) |

(52) U.S. Cl.
CPC ......... *C12Q 1/6816* (2013.01); *C12Q 1/6825* (2013.01); *C12Q 1/6888* (2013.01); *C12Q 1/689* (2013.01); *C12Q 1/701* (2013.01); *G01N 15/06* (2013.01); *G01N 15/1023* (2024.01); *G01N 15/1433* (2024.01); *G01N 15/1484* (2013.01); *G01N 33/487* (2013.01); *B01L 2200/141* (2013.01); *B01L 2300/069* (2013.01); *B01L 2400/0406* (2013.01); *G01N 15/075* (2024.01); *G01N 2015/1006* (2013.01); *Y02A 50/30* (2018.01)

(56) References Cited

U.S. PATENT DOCUMENTS

| | | |
|---|---|---|
| 6,797,817 B1 | 9/2004 | Eborsole |
| 2002/0173047 A1* | 11/2002 | Hudak ................. B01L 3/5023 |
| | | 436/178 |
| 2006/0246599 A1 | 11/2006 | Rosenstein |
| 2007/0218459 A1 | 9/2007 | Miller |
| 2009/0047673 A1 | 2/2009 | Cary |
| 2009/0246758 A1 | 10/2009 | Fiandaca |
| 2011/0117540 A1 | 5/2011 | Cary |
| 2012/0258469 A1 | 10/2012 | Babu |
| 2014/0370502 A1 | 12/2014 | Brennan |
| 2015/0322493 A1* | 11/2015 | Tulp ....................... C12Q 1/689 |
| | | 435/6.12 |
| 2016/0002621 A1* | 1/2016 | Nelson ............... C12N 15/1006 |
| | | 435/91.21 |

OTHER PUBLICATIONS

Crannell et al., "Nucleic Acid Test to Diagnose Cryptoporidiosis: Lab Assessment in Animal and Patient Specimens," Analytical Chemistry, vol. 86, pp. 2565-2571. (Year: 2014).*

International Search Report and Written Opinion for PCT/US16/32788 dated Aug. 25, 2016 (17 pages).

Pohlman, C. et al. A lateral flow assay for identification of *Escherichia coli* by ribosomal RNA hybridization, Analyst, 2014, 139, 1063-1071.

* cited by examiner

Pathogen list:
1. *Clostridium Difficile*
2. Shigella
3. Rotavirus
4. Cryptosporidium
5. Giardia
6. Salmonella
7. *Escherichia Coli*
8. Enterotoxigenic E.coli

SEQUENCE LISTING

<160> NUMBER OF SEQ ID NOS: 31

<210> SEQ ID NO 1
<211> LENGTH: 57
<212> TYPE: DNA
<213> ORGANISM: Clostridium difficile

<400> SEQUENCE: 1
tactgtccac atgtccttac ggtcatgctt caacccgtat gggaagctcc cctaccc      57

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gaaaaaaaag tagggagct tcccatacgg      30

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
catgaccgta aggacatgtg gaaaaaaaa      29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ccacatgtcc ttacggtcat gaaaaaaaa      29

<210> SEQ ID NO 5
<211> LENGTH: 57
<212> TYPE: DNA
<213> ORGANISM: Clostridium difficile

<400> SEQUENCE: 5
gggtagggga gcttcccata cgggttgaag catgaccgta aggacatgtg gacagta      57

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gaaaaaaaac cacatgtcct tacggtcatg                                    30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ccgtatggga agctccccta caaaaaaaa                                     29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8 gtagggagc ttcccatacg gaaaaaaaa                                      29

<210> SEQ ID NO 9
<211> LENGTH: 57
<212> TYPE: DNA
<213> ORGANISM: Zika Virus

<400> SEQUENCE: 9
ccttggcatg ctggggcaga caccggaact ccacactgga acaacaaaga gcactgg      57

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gaaaaaaaaa ctctttgttg ttccagtgtg g                                  31

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gtgtctgccc cagcatgcca aggtaaaaaa aa                                 32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
accttggcat gctggggcag acacaaaaaa aa                                 32

<210> SEQ ID NO 13

```
<211> LENGTH: 60
<212> TYPE: DNA
<213> ORGANISM: Salmonella enterica

<400> SEQUENCE: 13
cgaacgtatc acccaagaca actttacgga gttgacgatt gacggagcga agcgacgtca    60

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gaaaaaaaac ttcgctccgt caatcgtcaa                                      30

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
aagttgtctt gggtgatacg ttcgaaaaaa aa                                   32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cgaacgtatc acccaagaca acttaaaaaa aa                                   32

<210> SEQ ID NO 17
<211> LENGTH: 57
<212> TYPE: DNA
<213> ORGANISM: Eschericia coli

<400> SEQUENCE: 17
gggtagggga gcgttctgta agcctgcgaa ggtgtgctgt gaggcatgct ggaggta        57

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gaaaaaaaat acctccagca tgcctcacag                                      30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 19
tcgcaggctt acagaacgct caaaaaaaa                              29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
gagcgttctg taagcctgcg aaaaaaaaa                              29

<210> SEQ ID NO 21
<211> LENGTH: 57
<212> TYPE: DNA
<213> ORGANISM: Helicobacter pylori

<400> SEQUENCE: 21
tcactggtct agtggtcatg cgctgaaaat ataacggggc taagatagac accgaat    57

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gaaaaaaaat gtctatctta gccccgttat                             30

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gcgcatgacc actagaccag taaaaaaaa                              29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
actggtctag tggtcatgcg caaaaaaaa                              29

<210> SEQ ID NO 25
<211> LENGTH: 57
<212> TYPE: DNA
<213> ORGANISM: Helicobacter pylori

<400> SEQUENCE: 25
attcggtgtc tatcttagcc ccgttatatt ttcagcgcat gaccactaga ccagtga     57

<210> SEQ ID NO 26
<211> LENGTH: 30

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gaaaaaaaaa ctggtctagt ggtcatgcgc                                      30

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ataacggggc taagatagac accgaaaaaa aaaaa                                 35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ttcggtgtct atcttagccc ccgttataaa aaaaa                                 35

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ttcaacccgt atgggaagct caaaaaaaaa a                                     31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
aaaaaaaaaa tactgtccac atgtccttac g                                    31

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ggagcttccc atacgggttg aaaaaaaaaa                                      30
```

POINT OF NEED TESTING DEVICE AND METHODS OF USE THEREOF

CROSS-REFERENCE TO RELATED APPLICATIONS

This application is a division of U.S. patent application Ser. No. 15/574,750 filed Nov. 16, 2017, which application is a national stage filing under 35 U.S.C. § 371 of International Application No. PCT/US2016/032788, filed May 16, 2016, which claims priority to U.S. Provisional Application No. 62/162,668, filed on May 16, 2015, all of which are herein incorporated by reference in full.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

BACKGROUND

The present invention relates to methods, compositions, systems, and kits for rapidly detecting one or more nucleic acid target sequences from a plurality of biomarkers or a plurality of pathogens in a point-of-care (POC) or point-of-need (PON) setting. The notion behind POC and/or PON testing is to bring a diagnostic test conveniently and immediately to the patient, at the time and place of patient care and/or need. This increases the likelihood that the patient, physician, and clinical care team will receive the results in a faster time frame, which allows for more immediate clinical management decisions to be made.

SUMMARY OF THE INVENTION

Disclosed herein, in some embodiments, is a point of need testing device for detecting the presence of a target nucleic acid sequence in a biological sample from a subject, comprising: at least one lateral flow device, wherein said at least one lateral flow device comprises: (a) a sample loading area at one end of the lateral flow device, comprising a debris trapping material; (b) an area comprising a detectably labelled probe specific for a target nucleic acid sequence, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; and (d) absorbent material, wherein the absorbent material wicks, or is configured to wick an aqueous sample across the lateral flow device when the aqueous sample is added to the sample loading area. In some embodiments, said debris trapping material comprises glass fiber. In some embodiments, said at least one lateral flow device further comprises an area comprising a capture probe for a control nucleic acid sequence, wherein said control nucleic acid sequence is complementary to a sequence of the probe specific for the target nucleic acid sequence, wherein said capture probe for a control nucleic acid sequence is attached to the lateral flow device. In some embodiments, the detectably labelled probe specific for a target nucleic acid sequence is labeled with a moiety selected from a gold nanoparticle, a protein binding ligand, a hapten, an antigen, a fluorescent compound, a dye, a radioactive isotope and an enzyme. In some embodiments, the detectably labelled probe specific for a target nucleic acid sequence is labeled with a gold nanoparticle. In some embodiments, the capture probe is immobilized on the lateral flow device by covalent coupling. In some embodiments, the capture probe is immobilized on the lateral flow device by affinity binding. In some embodiments, the capture probe is attached to the lateral flow device by biotin: streptavidin affinity binding. In some embodiments, the capture probe is immobilized on the lateral flow device in the form of at least one dot or strip. In some embodiments, the lateral flow device comprises a solid support. In some embodiments, the solid support is selected from glass, paper, nitrocellulose and thread. In some embodiments, the target nucleic acid sequence is a nucleic acid sequence from a eukaryotic source. In some embodiments, the eukaryotic source is selected from algae, protozoa, fungi, slime molds and/or mammalian cells. In some embodiments, the target nucleic acid sequence is a nucleic acid sequence from a microorganism, virus or the microbiome. In some embodiments, the microorganism or virus is selected from *Escherichia, Campylobacter, Clostridium difficile*, Enterotoxigenic *E. coli* (ETEC), Enteroaggregative *Escherichia coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumonia*, flu, Zika, dengue, chikungunya, West Nile virus, Japanese encephalitis, malaria, HIV, H1N1, and *Clostridium difficile* resistant organisms. In some embodiments, the device comprises at least two, at least three, at least four, at least five, at least six, at least seven, at least eight, at least nine, at least ten, at least eleven, at least twelve, at least thirteen, at least fourteen, at least fifteen, at least twenty, or at least twenty five lateral flow devices. In some embodiments, each lateral flow device comprises probes specific for a different microorganism or virus. In some embodiments, the lateral flow devices are arranged in a radial manner. In some embodiments, the lateral flow devices are arranged in a radial manner around a central sample loading area. In some embodiments, the lateral flow devices are arranged in a lateral manner.

Disclosed herein in some embodiments, is a method for detecting the presence of target nucleic acid sequence in a biological sample from a subject, comprising: (i) lysing cells within the biological sample; (ii) adding the lysed sample to a sample loading area of a point of need testing device, wherein said point of need testing device comprises: at least one lateral flow device, wherein said at least one lateral flow device comprises: (a) a sample loading area at one end of the lateral flow device, comprising a debris trapping material; (b) an area comprising a detectably labelled probe specific for a target nucleic acid sequence, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; and (d) absorbent material, wherein the absorbent material wicks an aqueous sample across the lateral flow device when the aqueous sample is added to the sample loading area; and (iii) detecting a trimolecular hybridization of: (1) the target nucleic acid sequence, (2) the detectably labelled probe specific for the target nucleic acid sequence, and (3) the capture probe for the target nucleic acid sequence. In some embodiments, the target nucleic acid sequence is a nucleic acid sequence from a eukaryotic source. In some embodiments, the eukaryotic source is selected from algae, protozoa, fungi, slime molds and/or mammalian cells.

In some embodiments, disclosed herein is a method for detecting the presence of a microorganism or virus in a biological sample from a subject, comprising: (i) lysing cells within the biological sample; (ii) adding the lysed sample to a sample loading area of a point of need testing device, wherein said point of need testing device comprises: at least one lateral flow device, wherein said at least one lateral flow device comprises: (a) a sample loading area at one end of the lateral flow device, comprising a debris trapping material; (b) an area comprising a detectably labelled probe specific for a target nucleic acid sequence from a microorganism or virus, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; and (d) absorbent material, wherein the absorbent material wicks an aqueous sample across the lateral flow device when the aqueous sample is added to the sample loading area; and (iii) detecting a trimolecular hybridization of: (1) the target nucleic acid sequence, (2) the detectably labelled probe specific for the target nucleic acid sequence, and (3) the capture probe for the target nucleic acid sequence. In some embodiments, the target nucleic acid sequence is an rDNA or rRNA sequence. In some embodiments, the microorganism or virus is selected from *Escherichia, Campylobacter, Clostridium difficile*, Enterotoxigenic *E. coli* (ETEC), Enteroaggregative *Escherichia coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumoniae*, flu, Zika, dengue, chikungunya, West Nile virus, Japanese encephalitis, malaria, HIV, H1N1, and *Clostridium difficile* resistant organisms. In some embodiments, said debris trapping material comprises glass fiber. In some embodiments, nucleic acids are not isolated or purified from the lysed sample. In some embodiments, the biological sample is not subject to any further processing steps prior to or during the steps of the claimed method. In some embodiments, the cells are lysed with a lysis buffer comprising a chaotropic salt. In some embodiments, the biological sample from the subject is selected from stool, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mammary secretions, mucosal secretion, stool, stool water, pancreatic juice, lavage fluids from sinus cavities, bronchopulmonary aspirates, blastocyl cavity fluid, and umbilical cord blood. In some embodiments, the biological sample is a gastrointestinal fluid. In some embodiments, the biological sample is stool. In some embodiments, the biological sample is selected from, a skin swab sample, a throat swab sample, a genital swab sample and an anal swab sample. In some embodiments, the subject is a mammal. In some embodiments, the subject is human. In some embodiments, said at least one lateral flow device further comprises an area comprising a capture probe for a control nucleic acid sequence, wherein said control nucleic acid sequence is complementary to a sequence of the probe specific for the target nucleic acid sequence, wherein said capture probe for a control nucleic acid sequence is attached to the lateral flow device. In some embodiments, the detectably labelled probe specific for a target nucleic acid sequence is labeled with a moiety selected from a gold nanoparticle, a protein binding ligand, a hapten, an antigen, a fluorescent compound, a dye, a radioactive isotope and an enzyme. In some embodiments, the detectably labelled probe specific for a target nucleic acid sequence is labeled with a gold nanoparticle. In some embodiments, the capture probe is immobilized on the lateral flow device by covalent coupling. In some embodiments, the capture probe is immobilized on the lateral flow device by affinity binding. In some embodiments, the capture probe is attached to the lateral flow device by biotin: streptavidin affinity binding. In some embodiments, the capture probe is immobilized on the lateral flow device in the form of at least one dot or strip. In some embodiments, the lateral flow device comprises a solid support. In some embodiments, the solid support is selected from glass, paper, nitrocellulose and thread. In some embodiments, the point of need testing device comprises at least two, at least three, at least four, at least five, at least six, at least seven, at least eight, at least nine, at least ten, at least eleven, at least twelve, at least thirteen, at least fourteen, at least fifteen, at least twenty, or at least twenty five lateral flow devices. In some embodiments, each lateral flow device comprises a probe specific for a different microorganism or virus. In some embodiments, the lateral flow devices are arranged in a radial manner. In some embodiments, the lateral flow devices are arranged in a radial manner around a central sample loading area. In some embodiments, the lateral flow devices are arranged in a lateral manner.

Figure 4:
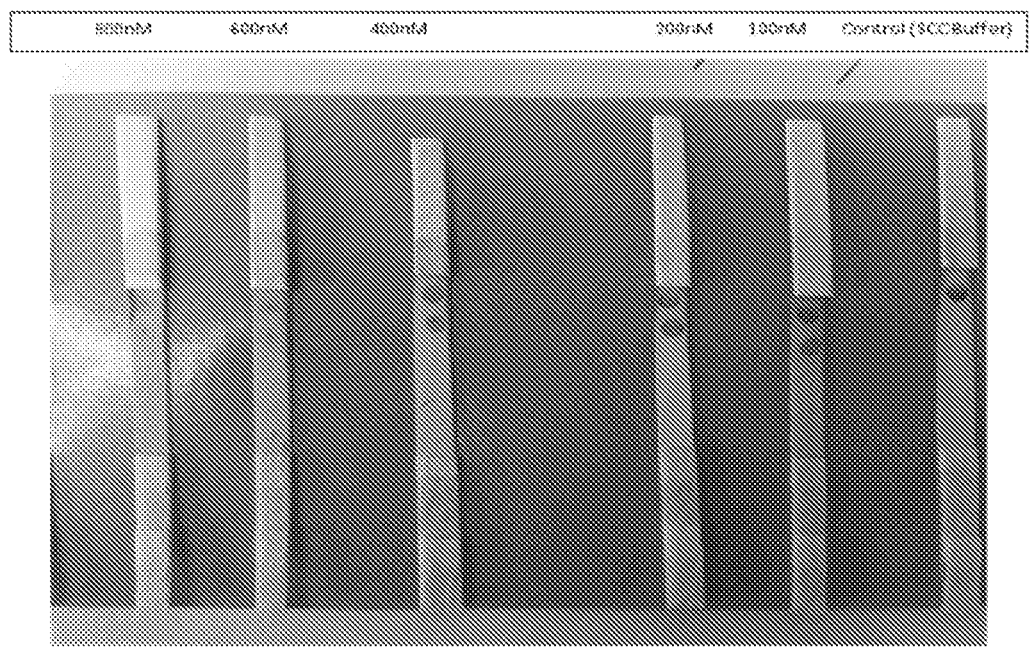

FIG. 4 exemplifies detection of *E. coli* sequence oligonucleotides that were added into stool. When a pea-sized stool sample (1 g) was spiked with *E. Coli* sequence-containing oligonucleotides and added to the sample loading glass fiber pad, the sample loading pad absorbed most of the impurities as shown by the clear nitrocellulose membrane. Any remaining impurities did not interfere with the hybridization of the probe conjugated with the gold nanoparticle. The stool was diluted in 4×SCC Buffer, 1×PBS Buffer and Laboratory Grade Water to run the assay successfully. Tween (2%) was used as a detergent with stool samples. The stool samples used were obtained using an IRB approved protocol 09-NR-N288.

Figure 5:
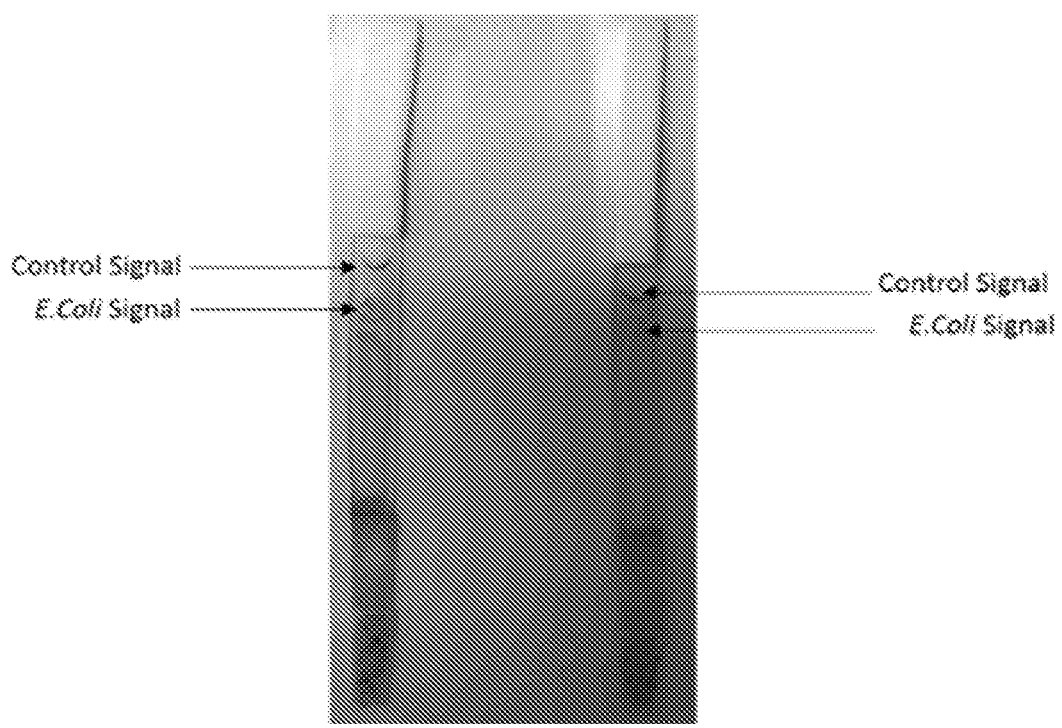

FIG. 5 exemplifies detection of endogenous *E. coli* in a stool sample. From left to right, the concentration of the stool sample in 1×PBS is 100 mg/ml and 50 mg/ml. 2% Tween was used as a detergent. The endogenous *E. coli* was detected directly from stool samples without RNA extraction. The Lateral Flow Assay designed for the detection of *E. coli* was tested on dilutions of endogenous stool in 1×PBS. The detection limit clearly decreased with the increase in the concentration of the stool. In addition, the high stool background appeared to limit the extraction of the GNP-conjugate probe from the fiber pad and introduce uneven flow patterns within the nitrocellulose. We diluted the stool in 4×SCC Buffer, 1×PBS Buffer and Laboratory Grade Water to run the assay successfully. Tween (2%) was used as a detergent with stool samples.

Figure 6:
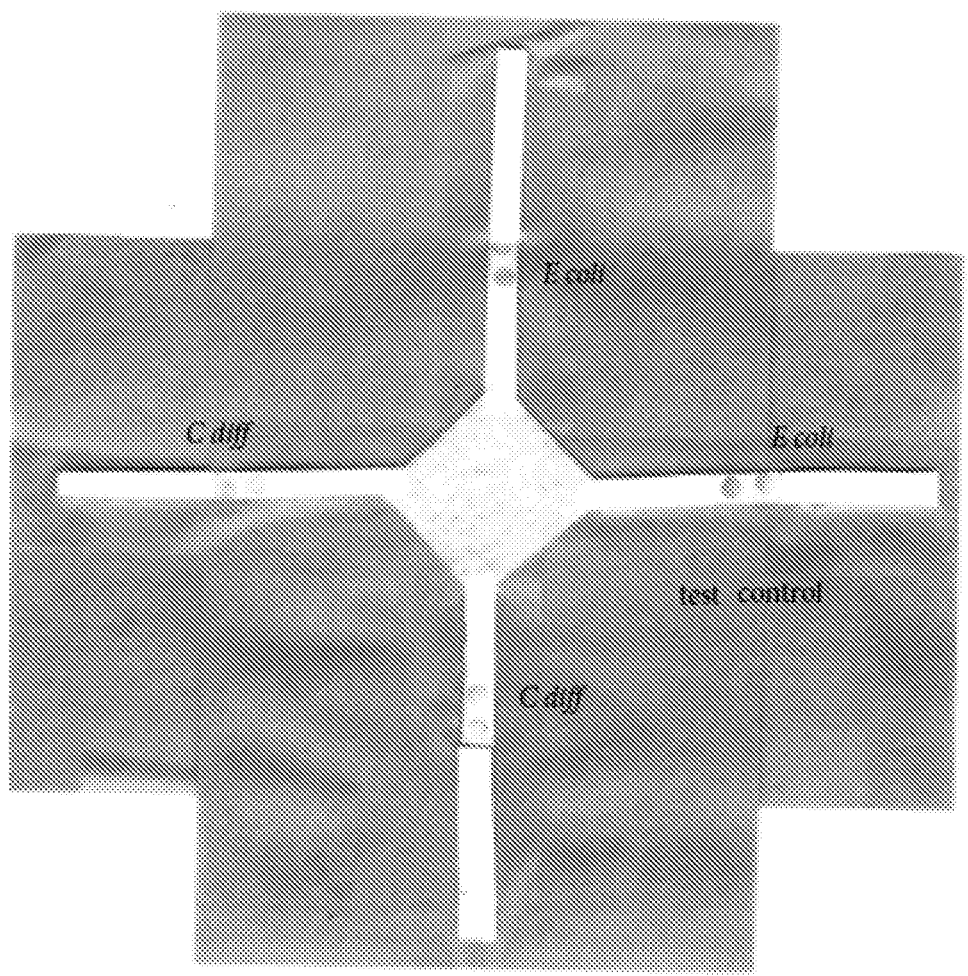

FIG. 6 exemplifies multiplex version of the lateral flow assay comprises multiple assays for different microbes arranged around a central sample (conjugate) pad. Four lateral flow assay strips (2×*E. coli* and 2×*C. diff*) are configured around a central sample pad. An adjusted volume of sample containing a mixture of *E. coli* and *C. diff* target sequences is dispensed onto the pad and as the sample is wicked along the assay strips the target sequences are efficiently detected as indicated by the red dots. Adjustment of the sample volume dispensed onto the sample pad must be made as the sample will be wicked along multiple strips. Since the sample volume for a single strip was 85 μL, a multiplex of four assays therefore required approximately 340 μL, of sample to be dispensed onto the sample pad.

DETAILED DESCRIPTION

Current methods of detecting pathogens involve molecular testing in the laboratory or rapid immunological tests. Rapid, point-of-care (POC) diagnostics are highly desirable in order to enable rapid medical treatment decisions in the clinic without delays awaiting laboratory testing. In addition, rapid POC tests are needed in remote or resource-limited settings (RLS) without access to laboratories, refrigeration, or electricity. However, the rapid POC immunological tests lack sensitivity and specificity. A rapid nucleic acid test (NAT) would have a higher sensitivity and specificity. To date, the most promising POC NAT tests involve isothermal amplification (e.g. Loop-mediated isothermal amplification (LAMP)) of target sequences that require enzymes (such as helicases or strand displacement) which need refrigeration and power supply for a heat source to maintain temperatures optimal for enzyme function. As such, isothermal amplification has shown considerable variability on the field. In contrast, there are NAT tests that do not rely on molecular amplification but rather on signaling a of a reporter group. One such reporter molecule with a high extinction coefficient is the gold nanoparticle. NAT tests may be read at the point-of-care (POC) using a lateral flow device.

The present invention relates to a method for performing target nucleic acid detection directly from a sample added to a testing device. In some embodiments, the methods involve multiplex nucleic acid detection. In some embodiments, the method is performed without a separate nucleic acid extraction or isolation step, and without enzyme or electricity-dependent methods such as PCR. In some embodiments the methods disclosed herein to not require molecular amplification or any laboratory instrumentation. Still further, the present invention relates to a sensitive multiplexed nucleic acid POC diagnostic paper strip device capable of detecting and identifying a multiplex of gene biomarkers for non-communicable chronic diseases such as cancers, autoimmune diseases, cardiovascular diseases, digestive diseases, metabolic diseases, neurological diseases, or a plurality of pathogens in infectious diseases, antibiotic susceptibility and antibiotic resistance markers, microbiome biomarkers, and relative abundance and diversity in the microbiome.

Point of Care and/or Need Device

Disclosed herein are point of care and/or need devices electricity free, low-cost devices that can be used for disease detection and health status monitoring in a low-resource setting.

Disclosed herein, in some embodiments, is a point of need device comprising at least one lateral flow device. In some embodiments, the device comprises at least two, at least three, at least four, at least five, at least six, at least seven, at least eight, at least nine, at least ten, at least eleven, at least twelve, at least thirteen, at least fourteen, at least fifteen, at least twenty, or at least twenty five lateral flow devices. In some embodiments, each lateral flow device detects a different target nucleic acid sequence (i.e., multiplex detection). The absence of antibody based conjugations or enzymes make the point of need device remarkably stable and durable under a range of environmental conditions.

Lateral Flow Device

Figure 1:
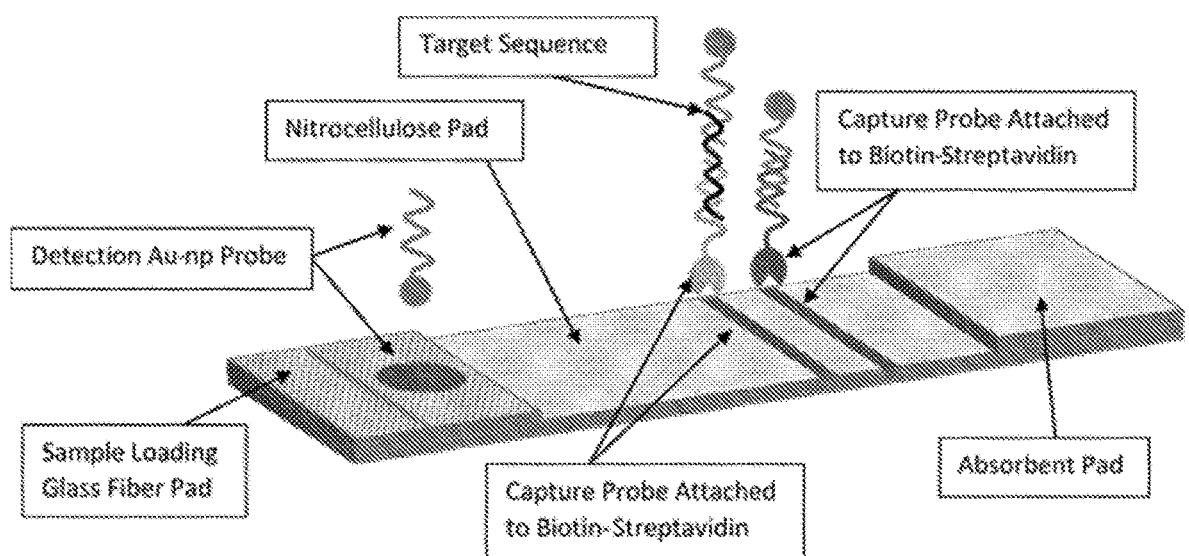
FIG. 1 schematically shows one embodiment of a lateral flow device, as disclosed herein. Biotinylated capture probes have oligonucleotide sequences that are complementary to a target pathogen rDNA or rRNA sequence. The biotinylated capture probe is conjugated with streptavidin and spotted on the test line. Gold conjugated detection probes are made up of sequences complementary to the adjacent regions on the target rDNA or rRNA sequence. The gold conjugated detection probe solution is deposited on the sample pad. A biotinylated control probe, which is complementary to the detection probe, is also conjugated with streptavidin and spotted on the test line. Gold conjugated detection probes which do not bind to a RNA or DNA target sequence bind to the spotted control probe on the test line resulting in a color change indicating positive technical integrity of the assay.
Figure 2:
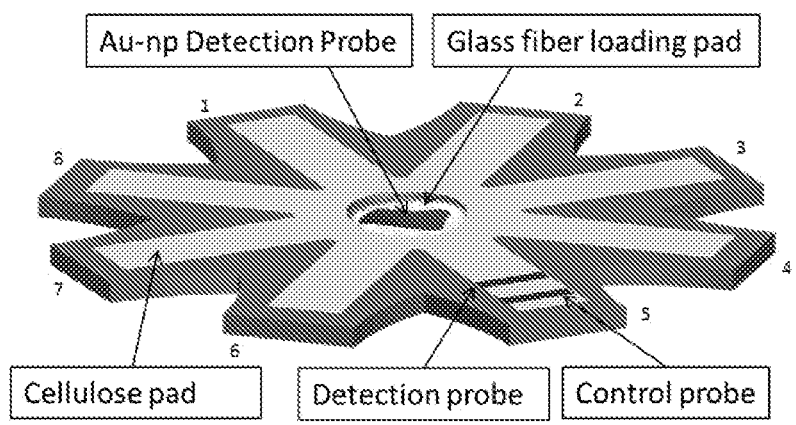
FIG. 2 exemplifies a multiplexed point of care device, comprising multiple lateral flow devices and capable of detection of multiple targets. In the exemplified embodiment, a plurality of nucleic acid targets are detected using multiple lateral flow devices micropatterned, cut or arranged into paper, nitrocellulose or thread.
Figure 3:
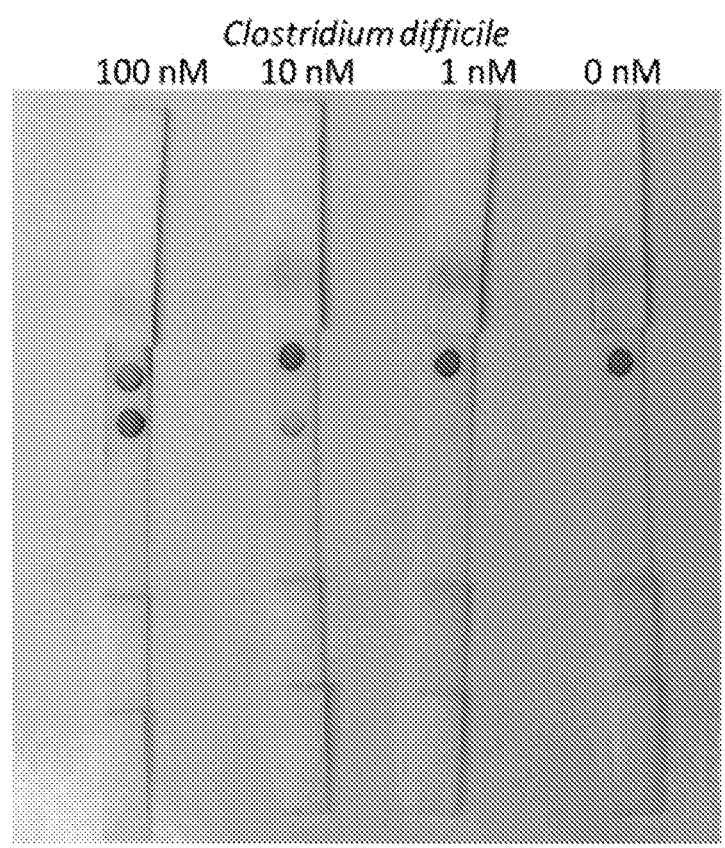
FIG. 3 exemplifies detection of a *C. diff* sequence oligonucleotide. About 85 μL of sample was added to the sample loading pad of a paper strip in a drop wise fashion. About 5 minutes was required for the sample to wick through the paper on a non-absorbent plastic sheet or wax paper in order to obtain a visual reading. Using synthetic oligonucleotide *C. diff* targets (23S rRNA), the limit of detection was 1 nM in 50 microliters of sample input. This corresponds to 50 fmoles of target, which is equivalent to $3 \times 10^{10}$ copies of RNA. Assuming there are $10^3$ 23 S rRNA per cell, we are able to detect $10^7$ bacterial cells. The signals can be amplified using silver or gold enhancement for a $10^3$ enhancement of signal. Thus, we are able to detect $10^4$ *C. diff.* cells per gram of stool which is the level found in clinical samples.

As disclosed herein, in some embodiments, a lateral flow device comprises: (a) a sample loading area at one end of the lateral flow device; (b) an area comprising a detectably labelled probe specific for a target nucleic acid sequence, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; and (d) absorbent material, wherein the absorbent material wicks an aqueous sample across the lateral flow device when the aqueous sample is added to the sample loading area. FIG. 1 discloses one embodiment of a lateral flow device, as disclosed herein.

Also disclosed herein, in some embodiments, a lateral flow device comprises: (a) a sample loading area at one end of the lateral flow device; (b) an area comprising a detectably labelled probe specific for a target nucleic acid sequence; (c) an area comprising a capture probe for the target nucleic acid sequence; and (d) absorbent material, wherein the absorbent material wicks an aqueous sample across the lateral flow device when the aqueous sample is added to the sample loading area. In some embodiments, the capture probe is capable of moving toward the area comprising the detectably labelled probe either by movement of the capture probe itself (i.e., the capture probe is not immobilized), or by movement of the area comprising the capture probe.

In some embodiments, the lateral flow device comprises a solid support. In some embodiments, the solid support is paper. In some embodiments, the solid support comprises cellulose, such as filter paper, chromatographic paper, nitrocellulose, and cellulose acetate. In some embodiments, the solid support comprises materials such as glass fibers, nylon, dacron, PVC, polyacrylamide, cross-linked dextran, agarose, polyacrylate, ceramic materials, and the like. In some embodiments, any material listed in this paragraph is specifically excluded from the solid support.

In some embodiments, the complete lateral flow device consists of an absorbent sample pad infused with the gold conjugated detection probe, a lateral flow channel which contains the spotted streptavidin fixed biotinylated capture probe on the test area and spotted streptavidin fixed biotinylated control probe on the control area.

Sample Loading Area

In some embodiments, the sample loading area comprises a material that traps debris within a (lysed or unlysed) biological sample. In some embodiments, the material comprises glass fiber. In some embodiments, the material comprises polyester and/or cellulose. In some embodiments, the material that traps debris is any commercially available microporous material. In some embodiments—any material listed in this paragraph is specifically excluded from the sample loading area.

As used herein, "traps" or "trapping" refers to immobilizing, delaying movement, capturing (temporarily or permanently), impeding movement, or hindering movement.

As used herein, "debris" within a biological sample refers to any solid particulate matter within a biological sample other than the components of the disclosed assays or devices. In some embodiments, "debris" includes tissue, food particles, clumped cells, cell walls, and the like.

In some embodiments, the sample loading area comprises at least one lysis or denaturing agent. In some embodiments, the lysis or denaturing agent is in the area where a sample is to be loaded. In some embodiments, the lysis or denaturing agent is in an area next to where a sample is to be loaded.

In some embodiments, the lysis or denaturing agent is a chaotropic salt. In some embodiments, the chaotropic salt is selected from guanidine thiocyanate, alkali metal perchlorates, alkali metal iodides, alkali metal trifluoroacetates, alkali metal trichloroacetates, and alkali metal thiocyanates. In some embodiments, the chaotropic salt is selected from urea, guanidine HCl, guanidine thiocyanate, guanidium thiosulfate, thiourea, or any combination thereof.

In some embodiments, the lysis or denaturing agent is a lytic enzyme. In some embodiments, the lytic enzyme is selected from the lytic enzyme is selected from the group consisting of beta glucurondiase, glucanase, glusulase, lysozyme, lyticase, mannanase, mutanolysin, zymolase, cellulase, lysostaphin, pectolyase, streptolysin O, and various combinations thereof.

In some embodiments, the lysis or denaturing agent is a detergent. In some embodiments, the detergent is Tween. In some embodiments, the detergent is selected from 3-[(3-cholamidopropyl)dimethylammonio]-1-propanesulfonate, octyl-(3-thioglucopyranoside, octyl-glucopyranoside, 3-(4-heptyl) phenyl 3-hydroxy propyl) dimethylammonio propane sulfonate, 34N,N-dimethyl(3-myristoylaminopropyl) ammoniolpropanesulfonate, 3-(decyldimethylammonio) propanesulfonate inner salt, 3-(dodecyldimethylammonio) propanesulfonate inner salt, 3-(N,N-dimethylmyristylammonio)propanesulfonate, n-dodecyl α-D-maltoside and combinations thereof.

In some embodiments, any of the listed lysis or denaturing agents is specifically excluded from the assays and devices disclosed herein.

Conjugation Area

The area comprising a detectably labelled probe specific for a target nucleic acid sequence, wherein said detectably labelled probe is not bound to the lateral flow device and is capable of wicking across the lateral flow device.

Detection Probe

In some embodiments, the detectably labelled probe specific for a target nucleic acid sequence is labeled with a moiety selected from a gold nanoparticle, a protein binding ligand, a hapten, an antigen, a fluorescent compound, a dye, a radioactive isotope and an enzyme. In some embodiments, the detectably labelled probe is labelled with a gold nanoparticle. In some embodiments, the detectably labelled probe is labelled with latex beads, latex microspheres and/or magnetic beads.

In some embodiments, the target nucleic acid sequence is a nucleic acid sequence from a eukaryotic source. In some embodiments, the eukaryotic source is selected from algae, protozoa, fungi, slime molds and/or mammalian cells.

In some embodiments, the target nucleic acid sequence is a nucleic acid sequence from a microorganism or virus. In some embodiments, the microorganism or virus is selected from *Escherichia, Campylobacter, Clostridium difficile*, Enterotoxigenic *E. coli* (ETEC), Enteroaggregative *Escherichia coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumoniae* flu, Zika, dengue, chikungunya, West Nile virus, Japanese encephalitis, malaria, HIV, H1N1, and *Clostridium difficile* resistant organisms. In some embodiments, the target nucleic acid sequence is from a microorganism or virus selected fromL DENV-1, DENV-2, DENV-3, DENV-4 NA (dengue), tcdA and tcdB (*C. diff* toxin genes), ZIKV RNA (Zika), CHIKV RNA, (chikungunya), Giar-4, Giar-6 (*Giardia lamblia*), invasion antigen loci (ial), invasion plasmid antigen H (ipa H) (*Shigella*), GARV, VP7, NSP3 (rotavirus), and HuNoV (norovirus). In some embodiments, any microorganism or virus listed herein is specifically excluded from the devices and methods disclosed herein.

In some embodiments, the target nucleic acid sequence is an rDNA or rRNA sequence from an organism. In some embodiments, the target nucleic acid sequence is an rRNA. In some embodiments, the rRNA is selected from 5 s, 16 s and 23 s rRNA. In some embodiments, the target nucleic acid sequence is selected from 5 s, 5.8 s, 28 s, and 18 s rRNA. In some embodiments, any embodiment listed herein is specifically excluded from the devices and methods disclosed herein.

In some embodiments, the target nucleic acid sequence is anywhere on the genome of a specific organism or virus that is specific to said organism or virus.

Choosing and designing the sequence of the probe specific for a target nucleic acid sequence is based on the nature of the source of the target nucleic acid sequence. Generally, the probe specific for the target nucleic acid that will be detectably labelled is capable of specifically hybridizing to part of the target nucleic sequence, separate from the sequence to which the capture probe will specifically hybridize.

Test Area

The area comprising a capture probe for the target nucleic acid sequence, wherein said capture probe for the target nucleic acid sequence is immobilized on the lateral flow device is also called the test area, or the test probe area. The test area can be in any form with well-defined boundaries, such as a dot, or a strip. In some embodiments, any embodiment listed herein is specifically excluded from the devices and methods disclosed herein.

In some embodiments, the capture probe is immobilized on the lateral flow device by covalent coupling.

In some embodiments, the capture probe is immobilized on the lateral flow device by affinity binding. In some embodiments, the capture probe is attached to the lateral flow device by biotin: streptavidin affinity binding.

Generally, the capture probe is capable of specifically hybridizing to part of the target nucleic acid sequence, separate from the sequence to which the detectably labelled probe will bind.

In some embodiments, any embodiment listed herein is specifically excluded from the devices and methods disclosed herein.

Control Area

In some embodiments, the point of need testing device disclosed herein comprises an area comprising a control probe, wherein said control probe is immobilized on the lateral flow device. This area is also called the control area, or the control probe area.

In some embodiments, the control probe comprises a sequence complementary to the detectably labelled probe.

In some embodiments, the control probe is immobilized on the lateral flow device by covalent coupling.

In some embodiments, the control probe is immobilized on the lateral flow device by affinity binding. In some embodiments, the control probe is attached to the lateral flow device by biotin: streptavidin affinity binding.

In some embodiments, any embodiment listed herein is specifically excluded from the devices and methods disclosed herein.

Absorbent Material

In some embodiments, the absorbent material which wicks an aqueous sample across the lateral flow device comprises cellulose. In some embodiments the cellulose is selected from filter paper, chromatographic paper, nitrocellulose, and/or cellulose acetate.

As used herein, a material that "wicks" an aqueous sample refers to any structure, material, and/or device, etc., that permits movement and/or transportation of an aqueous sample and at least some of its contents, or that permits the aqueous sample to contact the test and/or control areas of the disclosed devices.

In some embodiments, the absorbent material is in the form of an absorbent pad at the end of lateral flow device opposite of the sample loading area.

In some embodiments, the absorbent material runs the length of the lateral flow device.

In some embodiments, any embodiment listed herein is specifically excluded from the devices and methods disclosed herein.

Multiplex Detection Device

In some embodiments, the point of care device is capable of multiplex nucleic acid detection (i.e., the point of need testing device comprises at least two, at least three, at least four, at least five, at least six, at least seven, at least eight, at least nine, at least ten, at least eleven, at least twelve, at least thirteen, at least fourteen, at least fifteen, at least twenty, or at least twenty five lateral flow devices). In some embodiments, each lateral flow device comprises a probe specific for a different target nucleic acid (e.g., a different microorganism or virus).

In some embodiments, the plurality of lateral flow devices are arranged in a radial manner (i.e. similar to a star). In some embodiments, the lateral flow devices are arranged in a radial manner around a central sample loading area.

For example, in one embodiment the point of need device is a star-shaped multiplex paper strip. In some embodiments, thin sheets of porous nitrocellulose membranes are cut into star shapes using a computer-controlled X-Y knife plotter cutter. This device incorporates a knife in place of the traditional ink pen. The knife rotates freely on a turret, enabling precise cutting of various features. The control lines (containing the control probe) and test lines (containing the detection probe) will be spotted on each of the arms. The lateral flow paper strips are spotted using a BioDot AD1520 tabletop aspirating/dispensing workstation outfitted with two BioJet™ Elite dispensers capable of generating overlapping spots within nitrocellulose (minimal volumes of 20-50 nL) or continuous reagent lines (1 μL/cm). Dispensing protocols are custom written for the snowflake nitrocellulose design and optimized for buffer condition, dispense volume, and spatial separation.

In some embodiments, the plurality of lateral flow devices are arranged in a lateral manner.

In some embodiments, the plurality of lateral flow devices are micropatterned onto the point of care device by a method of patterning a porous, hydrophilic substrate into hydrophobic and hydrophilic regions. In some embodiments, such a method comprises disposing a wax material onto the hydrophilic substrate in a predetermined pattern; and heating the substrate to a temperature sufficient to melt the wax material, the melted wax material substantially permeating the thickness of the substrate and defining a pattern of one or more hydrophobic regions. Details of such a method can be found in International Patent Publication No. WO2010/102294, incorporated by reference herein.

In some embodiments, the plurality of nucleic acid target sequences are from gastrointestinal (GI) pathogens that cause diarrheal disease.

Kits

In some embodiments, disclosed herein is a kit useful for identifying the present of a target nucleic acid in a biological sample comprising at least one point of need device, as disclosed herein. In some embodiments, the point of need device is a multiplex detection device. In some embodiments, the kit further comprises reagents useful for practicing the methods disclosed herein, such as lysing buffer, dilution buffer, and/or a reagent for increasing the detectability of the detectably labeled probe.

Methods of the Invention

In some embodiments, the present invention relates to the detection of a plurality of nucleic acid sequences from a plurality of DNA or RNA targets in diverse human and animal samples without RNA or DNA extraction and without the use of enzymes or antibodies or instruments. The principal unique attribute of the assay is that it is an antibody and enzyme-free assay, requiring no assay critical mixing or conjugation of the substrate to be tested prior to assaying. Molecular amplification using isothermal enzymes or PCR is not required. Some or all of the components of the assay are pre-fixed on the strips, and all conjugation/binding between nucleic acids occur on the lateral flow device during the running of the assay itself. Another unique attribute is the minimal processing of the sample substrates. No molecular purification or substrate filtering is required. In some embodiments, the porous/spongy nature of the sample pad acts as a filter trapping particulate matter before the gold-conjugated detection probe solution flows down the lateral flow channel. As such, in some embodiments, the assay disclosed herein is a complete pre-prepared self-contained system in which several laboratory and physical steps are solved on the lateral flow device itself. The disclosed assays and devices can be used with or without lysing the cells within a biological sample.

In some embodiments, disclosed herein is a method for detecting presence of a target nucleic acid sequence in a biological sample from a subject, comprising: (i) contacting an unpurified biological sample that includes both a target nucleic acid sequence and other nucleic acids and cellular and other debris with a lateral flow device as disclosed herein; (ii) trapping said debris on one area or region of the device; and (iii) detecting hybridization of the target nucleic acid sequence with the detectably labelled probe.

In some embodiments, disclosed herein is a method for detecting presence of a target nucleic acid sequence in a biological sample from a subject, comprising: (i) contacting an unpurified biological sample that includes both a target nucleic acid sequence and other nucleic acids and cellular and other debris with a lateral flow device as disclosed herein; (ii) separating the debris from the target nucleic acid on the lateral flow device; and (iii) detecting hybridization of the target nucleic acid sequence with the detectably labelled probe.

Further disclosed herein, in some embodiments, is a method for detecting the presence of target nucleic acid sequence in a biological sample from a subject, comprising: (ii) adding the sample to a sample loading area of a point of need testing device, wherein said point of need testing device comprises: at least one lateral flow device, wherein said at least one lateral flow device comprises: (a) a sample loading area at one end (or region) of the lateral flow device, comprising a debris trapping material; (b) an area comprising a detectably labelled probe specific for a target nucleic acid sequence, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; (d) absorbent material, wherein the absorbent material wicks an aqueous sample across the lateral flow device when the aqueous sample is added to the sample loading area; and (iii) detecting a trimolecular hybridization of: (1) the target nucleic acid sequence, (2) the detectably labelled probe specific for the target nucleic acid sequence, and (3) the capture probe for the target nucleic acid sequence. In some embodiments, the cells in the sample are lysed prior to adding to the sample loading area. In some embodiments, the cells in the biological sample are not lysed. In some embodiments, the cells in the biological sample are lysed. In some embodiments, the cells in the sample are lysed on the sample loading area (i.e., the sample loading area comprises a lysis or denaturing agent).

In some embodiments, the methods disclosed herein do not comprise purification or isolation of nucleic acids before a biological sample is loaded onto a device, as disclosed herein.

In some embodiments, the methods disclosed herein do not comprise amplification of nucleic acids within a biological sample before they are loaded onto a device, as disclosed herein.

In some embodiments, the methods disclosed herein detect endogenous target nucleic acid sequence within an organism or virus within a biological sample.

In some embodiments, the target nucleic acid sequence is a nucleic acid sequence from a microorganism or virus. In some embodiments, the microorganism or virus is selected from *Escherichia, Campylobacter, Clostridium difficile*, Enterotoxigenic *E. coli* (ETEC), Enteroaggregative *Escherichia coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumonia*, flu, Zika, dengue, chikungunya, West Nile virus, Japanese encephalitis, malaria, HIV, H1N1, and *Clostridium difficile* resistant organisms. In some embodiments, the target nucleic acid sequence is from a microorganism or virus selected fromL DENV-1, DENV-2, DENV-3, DENV-4 RNA (dengue), tcdA and tcdB (*C. diff* toxin genes), ZIKV RNA (Zika), CHIKV RNA, (chikungunya), Giar-4, Giar-6 (*Giardia lamblia*), invasion antigen loci (ial), invasion plasmid antigen H (ipa H) (*Shigella*), GARV, VP7, NSP3 (rotavirus), and HuNoV (norovirus). In some embodiments, any microorganism or virus listed herein is specifically excluded from the devices and methods disclosed herein.

In some embodiments, the target nucleic acid sequence is an rDNA or rRNA sequence from an organism. In some embodiments, the target nucleic acid sequence is an rRNA. In some embodiments, the rRNA is selected from 5 s, 16 s and 23 s rRNA. In some embodiments, the target nucleic acid sequence is selected from 5 s, 5.8 s, 28 s, and 18 s rRNA. In some embodiments, any embodiment listed herein is specifically excluded from the devices and methods disclosed herein.

As used herein, a subject includes any animal for which diagnosis, screening, monitoring or treatment is contemplated. Animals include mammals such as primates and domesticated animals. In some embodiments, the subject is a human. In some embodiments, the subject is selected from a dog, a cat, a rabbit, a chicken, a cow, a sheep, and a horse. A patient refers to a subject such as a mammal, primate, human, or livestock subject afflicted with a disease condition or for which a disease condition is to be determined or risk of a disease condition is to be determined.

In some embodiments, the biological sample is selected from the group comprising any bodily fluid or tissue including but not limited to peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool, stool water, pancreatic juice, lavage fluids from sinus cavities, bronchopulmonary aspirates, blastocyl cavity fluid, or umbilical cord blood. The bodily fluid can be peripheral blood, sera, plasma, saliva or stool. The bodily fluid can be other than a gastrointestinal fluid, but in some embodiments gastric or fecal samples can be used. stool, urine, blood, cerebrospinal fluid, pus, amniotic fluid, tears, sputum, saliva, lung aspirate, vaginal discharge, mammary gland discharge, stool, a solid tissue sample, a skin swab sample, a throat swab sample and a genital swab sample. In some embodiments, the biological sample comprises cells in culture. In some embodiments, any biological sample listed is specifically excluded from the devices and methods disclosed herein.

Stool samples (as well as other body fluids and tissues) can be used with minimal preparation. Stool samples mixed in solution with either water or buffer are placed directly on the sample pad.

The sample to be tested is placed on the sample pad. The detectably labelled probes bind to the complementary region of available RNA or DNA target sequences. The solubilized bound and unbound detectably labelled probes, by diffusion and capillary action of the lateral flow channel, flow down the channel and over the capture probe area, and optionally, the control probes area. The immobilized capture probes bind to the adjacent complementary sequence of the RNA or DNA target sequence bound to the detectably labelled probes. This concentrates the detectably labeled probes so that they can be detected (e.g., if gold nanoparticle labeled probes are used, a red color will be visible when many of the gold nanoparticles are clumped together). The immobilized control probes capture unbound detectably labeled probes as they flow past.

Available target nucleic acid sequences can be increased by adding a lysing agent to the solution prior to placement on the sample pad. This increases the amount of molecular material available to bind to the detection probes. For rRNA targeted assays short incubation at high temperatures further improve assay sensitivity as this unfolds rRNA structures making more target sequence regions available to bind to detection probes.

In some embodiments, the target nucleic acid sequence is detected (i.e., a positive result is visible in the test capture probe area) in less than thirty minutes. In some embodiments, the target nucleic acids is detected in twenty five minutes or less, twenty minutes or less, fifteen minutes or less, or ten minutes or less. In some embodiments, the target nucleic acid sequence is detected within 1 to 5 minutes.

In some embodiments, detection of a positive result is accomplished visually. In some embodiments, visual detection is accomplished without additional instrumentation. In some embodiments, instrumentation can assist in detecting a positive result. For example, results can be quantified by imaging and analysis by computer. In some embodiments, the result can be scanned with a smartphone and electronically sent to a clinician. with a computer that has an adobe acrobat grayscale converter to quantify the visible light signal from the gold nanoparticle. Likewise, a color wheel for clear visualization of positive tests is available for RLS.

The practice of the present invention may employ, unless otherwise indicated, conventional techniques and descriptions of organic chemistry, polymer technology, molecular biology (including recombinant techniques), cell biology, biochemistry, and immunology, which are within the skill of the art.

In regards to design of the various probes disclosed herein, design of such probes are also within the skill of the art. For example, probe design strategy can be based on a combination of literature reading and looking in NCBI databases including "Blast" and "Gene" regarding an organism of interest. For example, a reading of the literature regarding stability and number of spores produced by bacteria could lead to a conclusion that 23S rRNA targeting would be best for spore-producing bacteria such as *Clostridium difficile*. As another example, a Zika nucleic acid sequence was available from the submission of a human-derived viral sequence submitted by the US Army to NCBI "Genebank" on 22 Mar. 2016.

Exemplary probes for use in the devices and methods disclosed herein are provided below (TS=Target Sequence; C=Capture Probe; D=Detection Probe; DC=Positive Control Probe; DTPA is dithiol phosphoramidite or S=S, Bio=Biotin)

```
Clostridium difficile #1:
TS= TAC TGT CCA CAT GTC CTT ACG GTC ATG CTT CAA CCC

GTA TGG GAA GCT CCC CTA CCC

C= /5BiosG/AA AAA AAA GTA GGG GAG CTT CCC ATA CGG

D= CAT GAC CGT AAG GAC ATG TGG AAA AAA AA/3DTPA/

DC= CCA CAT GTC CTT ACG GTC ATG AAA AAA AA/3Bio/

Clostridium difficile #2:
TS= GGG TAG GGG AGC TTC CCA TAC GGG TTG AAG CAT GAC

CGT AAG GAC ATG TGG ACA GTA

C= /5BiosG/AA AAA AAA CCA CAT GTC CTT ACG GTC ATG

D= CCG TAT GGG AAG CTC CCC TAC AAA AAA AA/3DTPA/

DC= GTA GGG GAG CTT CCC ATA CGG AAA AAA AA/3Bio/

Zika Virus
TS= CCTTGGCATGCTGGGGCAGACACCGGAACTCCACACTGGAACAACAA

AGAGCACTGG

C= /5BiosG/AAA AAA AAA CTC TTT GTT GTT CCA GTG TGG

D= GTG TCT GCC CCA GCA TGC CAA GGT AAA AAA AA/

3DTPA/

DC= ACC TTG GCA TGC TGG GGC AGA CAC AAA AAA AA/

3Bio/

Salmonella enterica serovar typhimirium
TS= CGAACGTATC ACCCAAGACAACT

TTACGGAGTTGACGATTGACGGAGCGAAGCGACGTCA

C= /5BiosG/AA AAA AAA CTT CGC TCC GTC AAT CGT CAA

D= AAG TTG TCT TGG GTG ATA CGT TCG AAA AAA AA/

3DTPA/

DC= CGA ACG TAT CAC CCA AGA CAA CTTAAA AAA AA/3Bio/

Eschericia coli
TS= GGG TAG GGG AGC GTT CTG TAA GCC TGC GAA GGT GTG

CTG TGA GGC ATG CTG GAG GTA

C= /5BiosG/AA AAA AAA TAC CTC CAG CAT GCC TCA CAG

D= TCG CAG GCT TAC AGA ACG CTC AAA AAA AA/3DTPA/

DC= GAG CGT TCT GTA AGC CTG CGA AAA AAA AA/3Bio/
```

```
Helicobacter pylori #1
TS= TCA CTG GTC TAG TGG TCA TGC GCT GAA AAT ATA ACG

GGG CTA AGA TAG ACA CCG AAT

C= /5BiosG/AA AAA AAA TGT CTA TCT TAG CCC CGT TAT

D= GCG CAT GAC CAC TAG ACC AGT AAA AAA AA/3DTPA/

DC= ACT GGT CTA GTG GTC ATG CGC AAA AAA AA/3Bio/

Helicobacter pylori #2
TS= ATT CGG TGT CTA TCT TAG CCC CGT TAT ATT TTC AGC

GCA TGA CCA CTA GAC CAG TGA

C= /5BiosG/AA AAA AAA ACT GGT CTA GTG GTC ATG CGC

D= ATA ACG GGG CTA AGA TAG ACA CCG AAA AAA AAA AA/

3DTPA/

DC= TTC GGT GTC TAT CTT AGC CCC CGT TAT AAA AAA AA/

3Bio/

Clostridium difficile #3
D= TTC AAC CCG TAT GGG AAG CTCAAAAAAAAAA-S=S

C= AAAAAAAAAATACTGTCCACATGTCCTTACG

DC= GGAGCTTCCCATACGGGTTGAAAAAAAAAA
```

EXAMPLES

Example 1: Preparation of Au-NP—rDNA or rRNA Conjugates

Final solution volumes: 1×=100 μL (10 strips), 5×=500 μL (50 strips), 10×=1 mL (100 strips). Micro centrifuge tubes were used for 1× use. For 5× and 10× use, 15 mL conical tubes were used. 15 mg of tris(2-carboxyethyl) phosphine hydrochloride (TCEP) powder was added to 50 μL RNAse/DNAse free water to produce a 1 M solution.

Note: This solution should be prepared fresh each for each reaction. 1 μL of 1 M TCEP (5×=54, 10×=10 μL) solution was added to 50 μL of disulfide detection primers (5×=250 μL, 10×=500 μL), vortexed lightly and incubated at 30 minutes RT. 50 μL of detection primers (5×=250 μL, 10×=500 μL) from the previous step was added to 1 mL 1 OD 15 nm gold nanoparticles (5×=5 mL, 10×=10 mL), and incubated for 16 hours at 4° C. Note: exposing the solution to light should be avoided. Optional: wrap container in aluminum foil to avoid light exposure. 1 μL of 10×PBS (5×=5 μL, 10×=10 μL) was added and the solution was incubated for 3-4 hours at 4° C. 2 μL of 10×PBS (5×=10 μL, 10×=100 μL) was then added and the solution was incubated for 3-4 hours at 4° C. 224 μL of 10×PBS (5×=1.12 mL, 10×=2.24 mL) was added and the solution was incubated overnight a 4° C. The resulting solution was vortexed on high for ten minutes.

For 5× and 10× use, solution was transferred to micro centrifuge tubes (5×=5 tubes, 10×=10 tubes). The tubes were centrifuged at full speed (20,000 rcf) for 15 minutes. Supernatant was removed and redispersed in 1 mL 1×PBS. The solution was again centrifuged and the step was repeated. After the second wash step, the supernatant was redispersed in 100 μL of GNP buffer: 20 mM NaPO4, 5% BSA, 0.25% Tween 20, and 10% sucrose. The tubes were then combined into one and stored at 4° C.

Example 2: Preparation of Capture/Control Probes 38.3 μL of 4 mg/mL streptavidin-PBS solution (at 4° C.) was added to 10.0 μL of 1 mM biotinylated Primers (in PBS, at 4° C.). An additional 41.7 μL of PBS was added. The solution was then incubated for 1 h at RT, then 10 μL of ethanol was added. The above was repeated for preparation of control probes. Final concentration of both capture and control probe should be 100 μM.

Example 3: Preparation of Strip

Sample pad: glass fiber, 1.0×30 cm: 20 μL of soak solution consisting of 0.25% Triton x-100, 0.15 M NaCl, and 0.05 M Tris HCl pH 8 was added to the sample pad. The sample pad was then dried at 37° C. for 2 h.

| For 1 mL stock solution | |
| --- | --- |
| Chemical | Volume (μL) |
| Tris-Cl 1M | 50 |
| NaCl 5M | 30 |
| Triton-X | 250 |
| Water | 670 |

Conjugate pad: glass fiber, 1.0×30 cm (GFCP203000, Millipore). Test Region: nitrocellulose, 2.0×30 cm (HFB24004, Millipore). Absorption pad: cellulose, 2.0×30 cm. All pieces were assembled onto plastic adhesive backing (6.1×30 cm), with each piece overlapping by 2 mm, except the conjugate pad overlapped with the sample pad by about 0.5 cm. The resulting material was then cut into strips with widths of approx. 3 mm. 0.65 μL, of both capture and control probe solution were added to the nitrocellulose membrane of strips. The control probe dot was placed directly before the absorbent pad, and the capture probe dot was placed about 2 mm before the control dot. The strip was dried at 37° C. for 2 h. 10 μL, of GNP conjugate (gold nanoparticle labelled probe) solution was added to the conjugate pad. The strip was then incubated at −20° C. for 15 min. Strips were then stored in a dry place at room temperature.

Example 4: Detection of Target Nucleic Acid

Approximately 300 mg of a stool sample (weight and volume may vary depending on consistency of specimen) was mixed with 1 ml of PBS buffer (water or SSC buffer can be used as well). Approximately 200 μL of Tween lysing detergent was added (other lysing reagents may also be used). The solution is well mixed. Denaturing an aliquot of the solution at 95° C. prior to assaying can improve sensitivity but is not essential for the assay. At least 85 μL of lysed stool solution was dispensed on to the sample loading pad (i.e., conjugate pad). The sample flowed down the strip and the capture probe and control probe dots were saturated with sample. Presence of the target sequence resulted in both the test probe dot and the control probe dot developing a red color. Lack of the target sequence resulted in only the control probe dot developing a red color. Color changes became visible after approximately 5 minutes. Color saturation was obtained at approximately 15 minutes.

The disclosures illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Other embodiments are set forth within the following claims.

What is claimed is:

1. A method for detecting the presence of a microorganism or virus in a diluted stool sample from a subject, comprising:
   (i) lysing cells within the diluted stool sample;
   (ii) adding the lysed sample to a sample loading area of a point of need testing device, wherein said point of need testing device comprises: at least one lateral flow device, wherein said at least one lateral flow device comprises:
   (a) a sample loading area positioned at one end of the lateral flow device, comprising a debris trapping material;
   (b) an area comprising a detectably labelled probe specific for a target nucleic acid sequence from a microorganism or virus, wherein said detectably labelled probe is not bound to the lateral flow device and is capable of wicking across at least a portion of the lateral flow device;
   (c) an area comprising a capture probe for the target nucleic acid sequence, wherein said capture probe for the target nucleic acid sequence is immobilized on the lateral flow device; and
   (d) absorbent material, wherein the absorbent material wicks an aqueous sample across the lateral flow device when the aqueous sample is added to the sample loading area; and
   (iii) detecting a trimolecular hybridization of: (1) the target nucleic acid sequence, (2) the detectably labelled probe specific for the target nucleic acid sequence, and (3) the capture probe for the target nucleic acid sequence,
   wherein nucleic acids are not isolated or purified from the lysed sample.

2. The method of claim 1, wherein the target nucleic acid sequence is an rDNA or rRNA sequence.

3. The method of claim 1, wherein the microorganism or virus is selected from *Escherichia, Campylobacter, Clostridium difficile*, Enterotoxigenic *E. coli* (ETEC), Enteroaggregative *Escherichia coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumoniae*, flu, Zika, dengue, chikungunya, West Nile virus, Japanese encephalitis, malaria, HIV, H1N1, and *Clostridium difficile* resistant organisms.

4. The method of claim 1, wherein said debris trapping material comprises glass fiber.

5. The method of claim 1, wherein the biological sample is not subject to any further processing steps prior to or during the steps of the claimed method.

6. The method of claim 1, wherein said at least one lateral flow device further comprises an area comprising a second capture probe for a control nucleic acid sequence, wherein said control nucleic acid sequence is complementary to a sequence of the probe specific for the target nucleic acid sequence, and wherein said second capture probe for a control nucleic acid sequence is attached to the lateral flow device.

7. The method of claim 1, wherein the detectably labelled probe specific for a target nucleic acid sequence is labeled with a moiety selected from a gold nanoparticle, a protein binding ligand, a hapten, an antigen, a fluorescent compound, a dye, a radioactive isotope and an enzyme.

8. The method of claim 1, wherein the point of need testing device comprises at least two lateral flow devices.

9. The method of claim 8, wherein each lateral flow device comprises a probe specific for a different microorganism or virus.

10. A method for detecting the presence of a target nucleic acid sequence in a diluted stool sample from a subject, the method comprising:
    (a) providing a point of need testing device comprising at least one lateral flow device, wherein said at least one lateral flow device comprises:
       (i) a sample loading area positioned at one end of the lateral flow device, comprising a debris trapping material;
       (ii) an area comprising a detectably labelled probe specific for a target nucleic acid sequence from a gastrointestinal pathogen, wherein said detectably labelled probe is not bound to the lateral flow device and is capable of wicking across at least a portion of the lateral flow device;
       (iii) an area comprising a first capture probe for the target nucleic acid sequence, wherein said first capture probe for the target nucleic acid sequence is immobilized on the lateral flow device;
       (iv) an area comprising a second capture probe for a control nucleic acid sequence, wherein said second capture probe comprises a portion of the target nucleic acid sequence from the gastrointestinal pathogen, wherein said control nucleic acid sequence is complementary to a sequence of the probe specific for the target nucleic acid sequence, and wherein said second capture probe for a control nucleic acid sequence is attached to the lateral flow device and
       (v) absorbent material, wherein the absorbent material wicks an aqueous sample across the lateral flow device when the aqueous sample is added to the sample loading area, wherein the presence of the target nucleic acid sequence is detected by trimolecular hybridization of: (1) the target nucleic acid sequence, (2) the detectably labelled probe specific for the target nucleic acid sequence, and (3) the first capture probe for the target nucleic acid sequence and the absence of the target nucleic acid sequence is detected by the bimolecular hybridization of (1) the detectably labelled probe specific for the target nucleic acid sequence and (2) the portion of the target nucleic acid sequence from the gastrointestinal pathogen of the second capture probe and
    wherein the target nucleic acid sequence from the gastrointestinal pathogen is an rDNA or rRNA sequence;
    (b) adding a diluted stool sample to the sample loading area; and
    (c) detecting a trimolecular hybridization of: (1) the target nucleic acid sequence, (2) the detectably labelled probe specific for the target nucleic acid sequence, and (3) the first capture probe for the target nucleic acid sequence or the bimolecular hybridization of (1) the detectably labelled probe specific for the target nucleic acid sequence and (2) the portion of the target nucleic acid sequence from the gastrointestinal pathogen of the second capture probe, wherein the diluted stool sample is an aqueous sample comprising unprocessed stool mixed with water and a lysis agent.

11. The method of claim 10, wherein the debris trapping material is infused with a detergent.

12. The method of claim 10, wherein the point of need testing device comprises at least two lateral flow devices and each lateral flow device comprises a probe specific for a different gastrointestinal pathogen.

* * * * *